US011918262B2

(12) United States Patent
Errico et al.

(10) Patent No.: US 11,918,262 B2
(45) Date of Patent: Mar. 5, 2024

(54) FIXATION DEVICE AND METHOD OF USING THE SAME

(71) Applicant: K2M, Inc., Leesburg, VA (US)

(72) Inventors: Thomas J. Errico, New York, NY (US); Peter Newton, La Jolla, CA (US); Harry Shufflebarger, Jupiter, FL (US); Brittany Harwell Lang, Warrenton, VA (US)

(73) Assignee: K2M, Inc., Leesburg, VA (US)

( * ) Notice: Subject to any disclaimer, the term of this patent is extended or adjusted under 35 U.S.C. 154(b) by 575 days.

(21) Appl. No.: 16/499,470

(22) PCT Filed: Mar. 30, 2018

(86) PCT No.: PCT/US2018/025382
§ 371 (c)(1),
(2) Date: Sep. 30, 2019

(87) PCT Pub. No.: WO2018/183833
PCT Pub. Date: Oct. 4, 2018

(65) Prior Publication Data
US 2020/0253655 A1 Aug. 13, 2020

Related U.S. Application Data

(60) Provisional application No. 62/478,701, filed on Mar. 30, 2017.

(51) Int. Cl.
*A61B 17/86* (2006.01)
*A61B 17/56* (2006.01)

(52) U.S. Cl.
CPC ...... *A61B 17/8635* (2013.01); *A61B 17/8685* (2013.01); *A61B 2017/564* (2013.01); *A61B 2017/8655* (2013.01)

(58) Field of Classification Search
CPC .............. A61B 17/8685; A61B 17/864; A61B 17/8655; A61B 17/863; A61B 17/844;
(Continued)

(56) References Cited

U.S. PATENT DOCUMENTS 80,560 A * 8/1868 Nagle ................... F16B 13/124
411/80.6
137,338 A * 4/1873 Bartlett ................. F16B 13/124
411/63
(Continued)

FOREIGN PATENT DOCUMENTS

WO 2018136602 A1 7/2018

OTHER PUBLICATIONS

International Search Report for Application No. PCT/US2018/025382 dated Jul. 9, 2018, 2 pages.

*Primary Examiner* — David W Bates
(74) *Attorney, Agent, or Firm* — Lerner David LLP

(57) ABSTRACT

A fixation device includes an outer member, an inner member, and an expansion member. The outer member includes an elongated body portion and a slotted tail portion, and defines a central bore therethrough that extends along a central longitudinal axis. The inner member is disposed within the central bore of the outer member, and the expansion member is coupled to the inner member. Proximal movement of the inner member relative to the outer member moves the expansion member into the slotted tail portion of the outer member such that the slotted tail portion moves from an undistended configuration to a distended configuration.

16 Claims, 6 Drawing Sheets

(58) Field of Classification Search
CPC .. A61C 8/0033; F16B 13/068; F16B 13/0816; F16B 13/0833; F16B 13/0841; F16B 13/0866; F16B 13/124
See application file for complete search history.

(56) References Cited

U.S. PATENT DOCUMENTS

| | | | | |
|---|---|---|---|---|
| 1,011,398 A * | 12/1911 | Andregg | F16B 13/124 411/63 |
| 1,051,444 A * | 1/1913 | Pleister | F16B 13/124 411/80.5 |
| 1,057,975 A * | 4/1913 | Newhall et al. | F16B 13/124 411/80.5 |
| 1,116,545 A * | 11/1914 | Barrett | F16B 13/124 411/72 |
| 1,130,003 A * | 3/1915 | Masor | F16B 13/124 411/68 |
| 1,136,638 A * | 4/1915 | Zifferer | F16B 13/124 411/80.5 |
| 1,234,487 A * | 7/1917 | Raeger | F16B 13/124 279/104 |
| 1,248,008 A * | 11/1917 | Pleister | F16B 13/124 411/80.5 |
| 1,267,903 A * | 5/1918 | Pleister | F16B 13/124 411/80.5 |
| 2,397,545 A * | 4/1946 | Hardinge | A61B 17/746 606/68 |
| 2,490,364 A * | 12/1949 | Livingston | A61B 17/7266 606/68 |
| 3,708,883 A * | 1/1973 | Flander | A61C 8/0075 433/174 |
| 3,974,735 A * | 8/1976 | Berner | F16B 13/066 411/41 |
| 4,013,071 A * | 3/1977 | Rosenberg | A61B 17/8685 411/397 |
| 4,091,806 A * | 5/1978 | Aginsky | A61B 17/7225 606/63 |
| RE33,348 E * | 9/1990 | Lower | A61B 17/8685 606/86 R |
| 5,209,753 A * | 5/1993 | Biedermann | A61B 17/8685 606/314 |
| 5,489,210 A * | 2/1996 | Hanosh | A61C 8/0033 433/173 |
| 5,713,903 A * | 2/1998 | Sander | A61F 2/0811 606/326 |
| 5,725,581 A * | 3/1998 | Brånemark | A61B 17/8625 411/386 |
| 5,928,244 A * | 7/1999 | Tovey | A61F 2/0811 606/104 |
| 6,129,763 A * | 10/2000 | Chauvin | A61F 2/4455 623/17.11 |
| 6,168,597 B1 | 1/2001 | Biedermann et al. | |
| 6,436,100 B1 * | 8/2002 | Berger | A61B 17/864 411/394 |
| 8,388,660 B1 * | 3/2013 | Abdou | A61B 17/8685 606/267 |
| 8,814,919 B2 | 8/2014 | Barrus et al. | |
| 8,870,877 B2 * | 10/2014 | Koogle, Jr. | A61F 2/0811 606/86 R |
| 9,211,153 B2 * | 12/2015 | Fisher | A61B 17/8625 |
| 9,393,049 B2 | 7/2016 | Jones et al. | |
| 10,736,683 B2 * | 8/2020 | Garvey | A61B 17/686 |
| 2003/0045881 A1 * | 3/2003 | Barouk | A61B 17/863 606/317 |
| 2004/0068261 A1 * | 4/2004 | Fourcault | A61B 17/863 606/67 |
| 2009/0105771 A1 | 4/2009 | Lei et al. | |
| 2009/0281580 A1 * | 11/2009 | Emannuel | A61B 17/8685 606/304 |
| 2010/0190138 A1 * | 7/2010 | Giorno | A61B 17/863 433/174 |
| 2010/0304333 A1 * | 12/2010 | Ghavidel | A61C 8/005 433/173 |
| 2011/0054542 A1 * | 3/2011 | Kevin | A61B 17/8052 606/70 |
| 2012/0010668 A1 * | 1/2012 | Shimko | A61B 17/8685 606/313 |
| 2012/0064488 A1 | 3/2012 | Lazarof | |
| 2014/0107713 A1 * | 4/2014 | Pech | A61B 17/844 606/313 |
| 2014/0249579 A1 | 9/2014 | Heaven et al. | |
| 2014/0257413 A1 * | 9/2014 | Appenzeller | A61B 17/866 606/86 R |
| 2014/0356812 A1 * | 12/2014 | Anderson | A61C 8/0016 433/173 |
| 2017/0112552 A1 * | 4/2017 | Sinnott | A61B 17/7233 |
| 2017/0119503 A1 * | 5/2017 | Kim | A61C 8/0033 |
| 2017/0266007 A1 * | 9/2017 | Gelaude | A61B 34/10 |
| 2018/0252251 A1 * | 9/2018 | Huang | F16B 15/06 |
| 2018/0303529 A1 * | 10/2018 | Zastrozna | A61B 17/864 |
| 2019/0070009 A1 * | 3/2019 | Champagne | A61F 2/4225 |

* cited by examiner

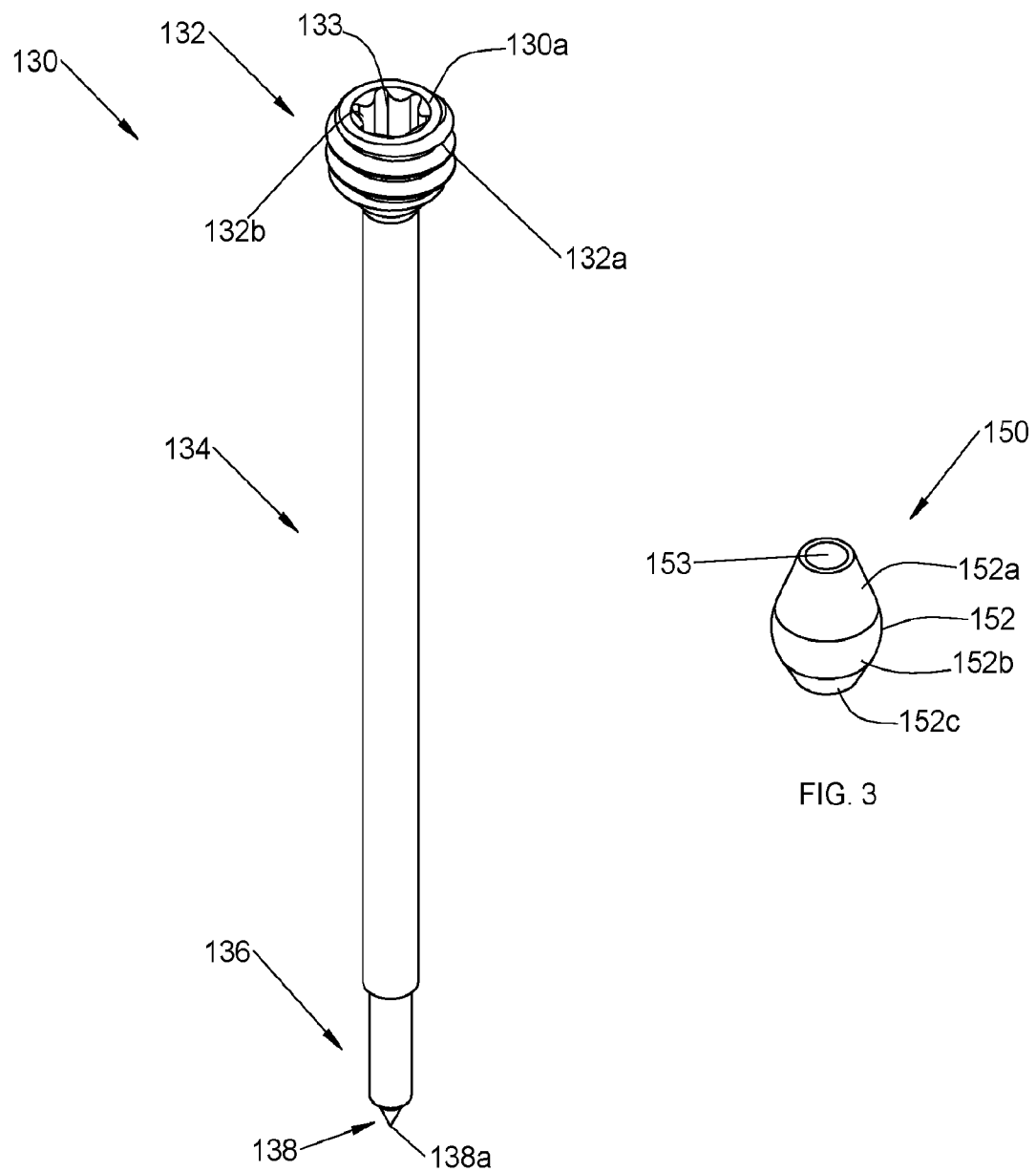

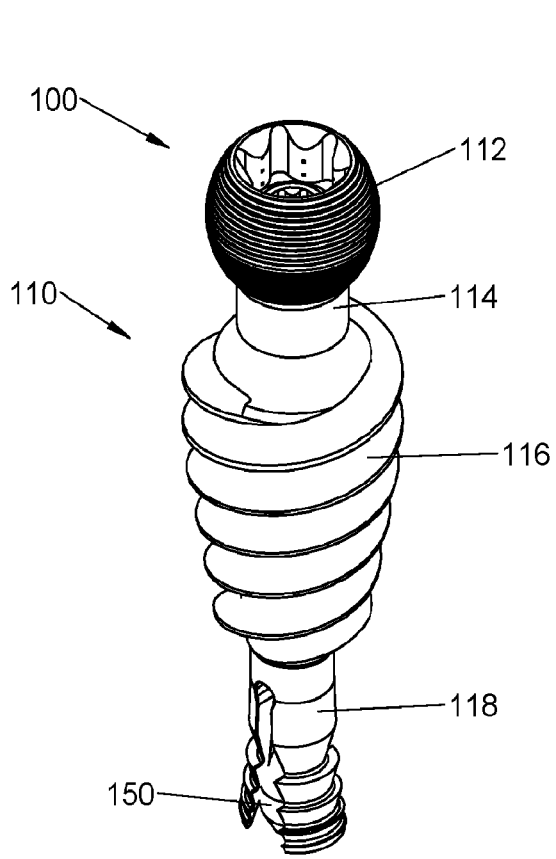
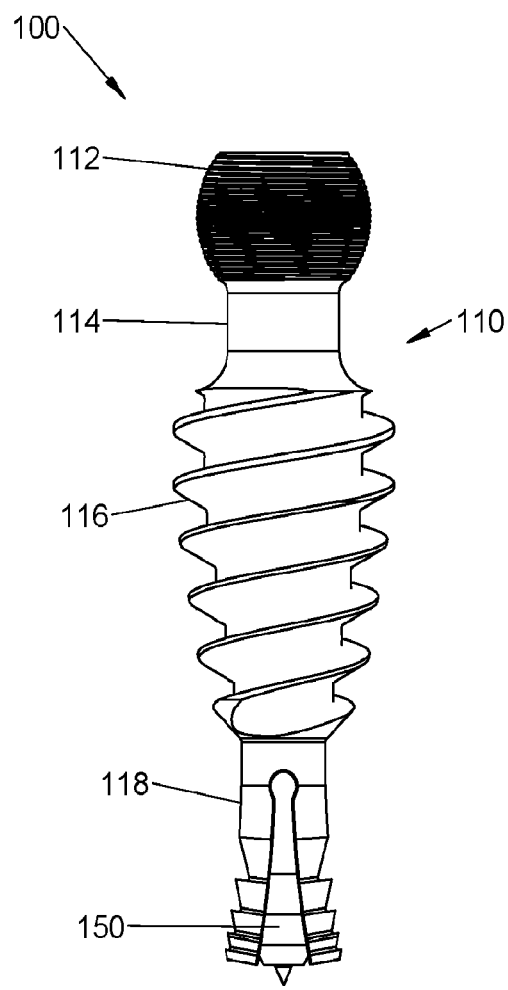
FIG. 4A
FIG. 4B

FIXATION DEVICE AND METHOD OF USING THE SAME

CROSS-REFERENCE TO RELATED APPLICATION

This application is a national phase entry under 35 U.S.C. § 371 of International Application No. PCT/US2018/025382, filed Mar. 30, 2018, which claims the benefit of the filing date of U.S. Provisional Patent Application No. 62/478,701, filed Mar. 30, 2017, the disclosures of which are hereby incorporated herein by reference.

TECHNICAL FIELD

The present disclosure relates generally to surgical devices, and more particularly, to fixation devices with distensible ends and methods for securing the fixation devices to osseous tissue.

BACKGROUND

Spinal pathologies, whether the result of genetic or developmental irregularities, trauma, chronic stress, tumors, or disease can limit the spine's range of motion or threaten critical elements of the nervous system housed within the spine. A variety of systems to correct the alignment of the spinal vertebrae involving the implantation of artificial assemblies in or on the spine have been devised.

The mechanical hardware used to immobilize the spinal column typically involves a series of bone screws and metal rods or plates. When the spine surgery is performed posteriorly, it is common practice to place bone screws into the vertebral bodies and then connect a metal rod between the bone screws, thus creating a rigid structure between adjacent vertebral bodies. In some cases, these devices may be permanently implanted in the patient. In other cases, the devices may be implanted only as a temporary means of stabilizing or fixing the bones or bone fragments, with subsequent removal when no longer needed.

When using bone screws, a clinician directs the bone screw into a vertebra. The vertebra is composed of a hard, strong ossified shell surrounding soft osseous tissue. The pedicle is a narrow passage way which connects proximal and distal sides of the vertebra through the vertebral body. The pedicle is a challenging area for the clinician to traverse since the spinal cord, a very delicate tissue and nerve connector for the entire body, is located medial to the pedicle. There are also nerve roots and organs extending lateral to the pedicle. Therefore, a clinician puts care into directing the bone screw in the correct path through the vertebra. Sometimes a clinician may want to redirect the bone screw, in which case the clinician would need to remove the original bone screw, and redirect the bone screw through the pedicle. Redirection removes more bone and can compromise fixation of the bone screw or completely damage the vertebral body, rendering it unusable as a point of device fixation.

Therefore, a fixation device that can help a clinician improve efficiency and/or accuracy of inserting fixation devices, such as a bone screws, into a vertebra, while also protecting the spinal cord and minimizing the need for redirection is desirable.

SUMMARY

In accordance with an aspect of the present disclosure, a fixation device includes an outer member, an inner member, and an expansion member. The outer member includes an elongated body portion and a slotted tail portion, and defines a central bore therethrough that extends along a central longitudinal axis. The inner member is disposed within the central bore of the outer member, and the expansion member is coupled to the inner member. Proximal movement of the inner member relative to the outer member moves the expansion member into the slotted tail portion of the outer member such that the slotted tail portion moves from an undistended configuration to a distended configuration.

The outer member may include a head portion defining an opening therein that is in fluid communication with the central bore. The inner member may be disposed within the central bore distal to the opening defined in the head of the outer member and the inner member may be movable longitudinally within the central bore.

The elongated body portion of the outer member may taper distally towards the slotted tail portion. The elongated body portion may include helical threads disposed on an outer surface thereof.

The slotted tail portion may include at least one slit defined therein. The at least one slit may extend longitudinally through at least a portion of a length of the slotted tail portion and may be open at a distal end of the outer member. In some embodiments, the at least one slit of the slotted tail portion includes two slits disposed on opposed sides of the slotted tail portion. The slotted tail portion may include concentric arcs extending from an outer surface thereof.

The central bore may include a first portion, a second portion having a diameter smaller than a diameter of the first portion, and a third portion having a varying diameter.

The inner member may include a head, a proximal shaft, and a distal shaft. The head of the inner member may be positioned within a first portion of the central bore, the proximal shaft may be positioned within a second portion of the central bore, and the distal shaft may be secured within the expansion member, the expansion member positionable within a third portion of the central bore. The inner member may include a distal tip extending distally through the expansion member. In some embodiments, the head of the inner member includes a threaded outer surface threadingly engaged with a threaded inner surface of the outer member defining the first portion of the central bore.

The expansion member may include a body having a proximal portion and a distal portion. A diameter of the distal portion may be wider than a diameter of the proximal portion such that when the slotted tail portion is in the distended configuration, the distal portion of the expansion member exerts a radial force on the slotted tail portion.

In accordance with an aspect of the present disclosure, a method of securing a fixation device to osseous tissue includes: inserting an elongated body portion and a slotted tail portion of an outer member of a fixation device into a hole in osseous tissue, the slotted tail portion disposed in an undistended configuration, the outer member defining a central bore therethrough extending along a central longitudinal axis; and applying a force to an inner member of the fixation device that is disposed within the central bore of the outer member, the inner member coupled to an expansion member such that the force applied to the inner member moves the expansion member proximally into the slotted tail portion to move the slotted tail portion to a distended configuration.

In embodiments, applying the force to the inner member includes rotating the inner member.

The method may further include applying a rotational force to the outer member to engage helical threads disposed on an outer surface of the elongated body portion with the osseous tissue.

Other aspects, features, and advantages will be apparent from the description, drawings, and the claims.

BRIEF DESCRIPTION OF THE DRAWINGS

The accompanying drawings, which are incorporated in and constitute a part of this specification, illustrate embodiments of the present disclosure and, together with a general description of the disclosure given above, and the detailed description of the embodiments given below, serve to explain the principles of the present disclosure, wherein:

FIG. 2 is a perspective view of an inner member of the fixation device of FIGS. 1A and 1B;

FIG. 3 is a perspective view of an expansion member of the fixation device of FIGS. 1A and 1B;

FIG. 4A is a perspective view of the fixation device of FIG. 1A, shown in an expanded position;

FIG. 4B is a side view of the fixation device of FIG. 4A;

DETAILED DESCRIPTION

Figure 1A:
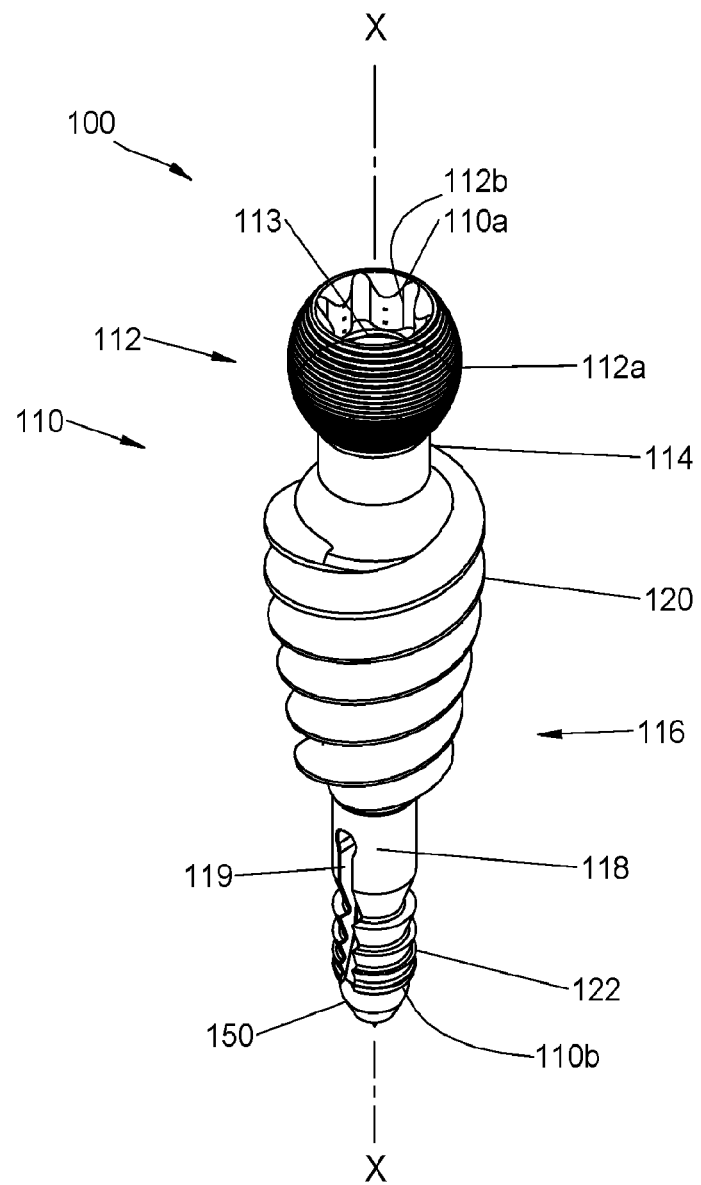
FIG. 1A is a perspective view of a fixation device in accordance with an embodiment of the present disclosure, shown in an unexpanded position.

Exemplary embodiments of the present disclosure are discussed herein below in terms of a fixation device for use in osseous tissue. While the principles of the present disclosure are described below with respect to the insertion of the fixation device into a pedicle of a vertebra during orthopedic spine surgery, it should be understood that the fixation device of the present disclosure is suitable for insertion into any osseous tissue, such as the iliac of the pelvis, and use in a variety of surgical procedures. Accordingly, a person of ordinary skill in the art will readily appreciate that the size and/or shape of the fixation device, or components thereof, can be modified for proper alignment and fit within a desired osseous tissue. For example, the fixation device may be shorter in length than a traditional bone screw. As another example, if the osseous tissue is a pedicle of a vertebra, the fixation device can be sized and dimensioned so that it would not extend into the intervertebral space.

Embodiments of the present disclosure will now be described in detail with reference to the drawings in which like reference numerals designate identical or corresponding elements in each of the several views. Throughout this description, the term "proximal" refers to a portion of a device, or component thereof, that is closer to a clinician, and the term "distal" refers to the portion of the device, or component thereof, that is farther from the clinician. The term "clinician" refers to a doctor (e.g., a surgeon), a nurse, or any other care provider, and may include support personnel.

Figure 1B:
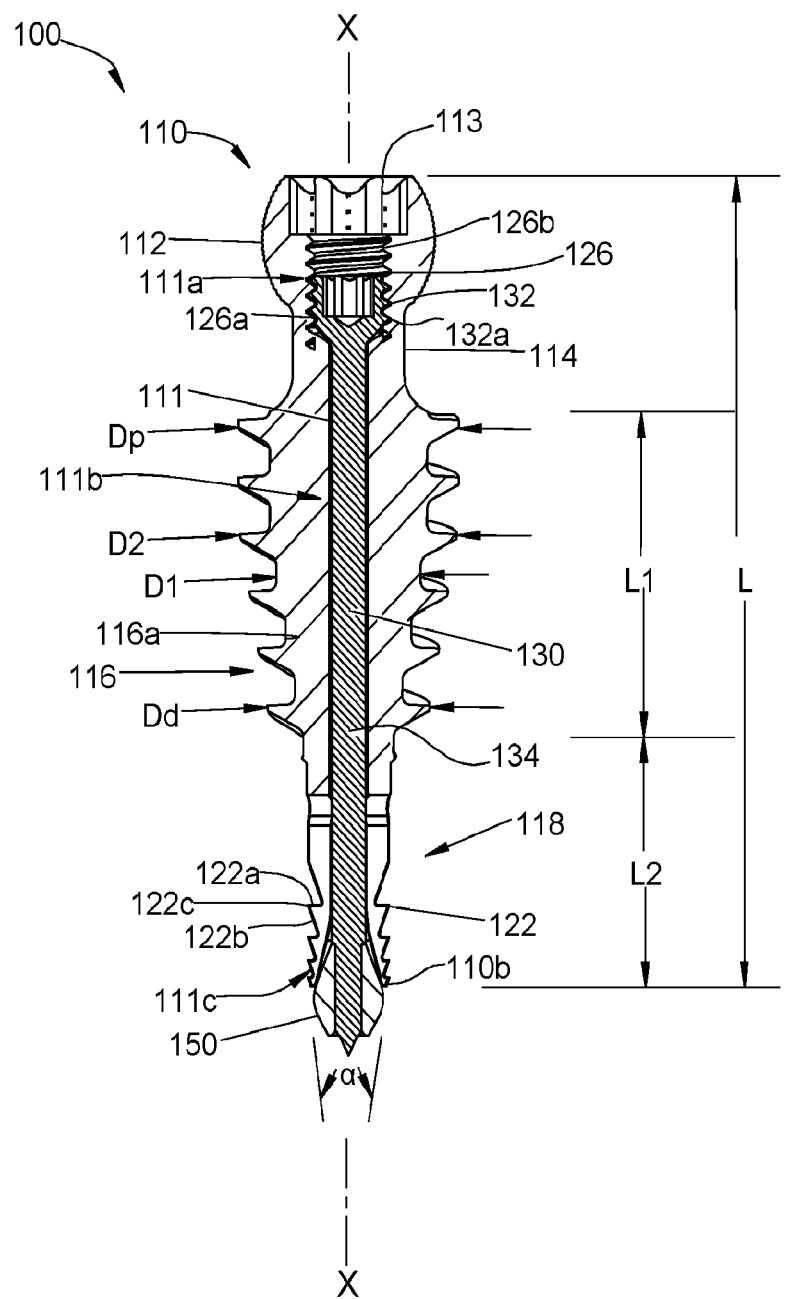
FIG. 1B is a cross-sectional view of the fixation device of FIG. 1A.

Referring now to FIGS. 1A and 1B, a fixation device or rivet 100 in accordance with an embodiment of the present disclosure is shown. The fixation device 100 includes an outer member or post 110, an inner member or pin 130, and an expansion member or bulb 150. The fixation device 100 is suitable for use during the treatment of bones (e.g., to fix the position of a bone, or portions thereof, or to maintain alignment of bone(s)), and may provide a point of fixation and/or facilitate the attachment of other devices (e.g., rods, plates, etc.) to the bone(s).

The outer member 110 extends along a central longitudinal axis "X" and includes a head portion 112, a neck portion 114, an elongated or tapered body portion 116, and a slotted tail portion 118. The outer member 110 may be integrally formed (e.g., by machining, molding, etc.), or one or more of the head portion 112, the neck portion 114, the tapered body portion 116, and/or the slotted tail portion 118 may be fixedly attached (e.g., by welding, fastening, press-fitting, etc.) to an adjacent component of the outer member 110 such that the outer member 110 has a one-piece construction.

The head portion 112 of the outer member 110 has a substantially spherical or ball shape. The head portion 112 includes an outer surface 112a that is roughened (e.g., textured, grooved, etc.) to enhance the grip of a clinician or the attachment of another surgical device thereto, such as a modular screw assembly (not shown) which, in turn, may be coupled to other surgical devices (e.g., rods, plates, etc.). Suitable modular screw assemblies include, for example, taper lock or set screw housing systems such as those shown in U.S. Pat. Nos. 8,814,919 and 9,393,049, and/or modular head assemblies such as those shown in Int'l Appl. No. PCT/US18/14179, the entire content of each of which is incorporated by reference herein. The head portion 112 can be of any shape and/or size suitable for manipulating the fixation device 100 into an osseous tissue and/or facilitating attachment of other surgical devices thereto.

The head portion 112 includes an opening 113 therein that is defined by an inner surface 112b of the head portion 112. The opening 113 is disposed at a proximal end 110a of the outer member 110 and is configured and dimensioned to receive a driving instrument (not shown). The inner surface 112b may be multi-faceted (e.g., hexagonal or hexolobular in shape), keyed, or any other suitable configuration that is engageable with a suitable driving instrument to enable the driving instrument to control rotation of the outer member 110 and/or aid in the insertion or removal of the outer member 110 into or out of osseous tissue.

The neck portion 114 extends between the head portion 112 and the tapered body portion 116. The neck portion 114 has an outer transverse dimension (e.g., diameter) that is smaller than the outer transverse dimensions of the head portion 112 and the tapered body portion 116 to separate the head portion 112 which, as described above, may act as a connection portion of the fixation device 100 to other surgical devices, and the tapered body portion 116 which acts as an anchoring portion of the fixation device 100 in the osseous tissue. This allows securing the fixation device 100 into bone and subsequently attaching a modular head assembly (see e.g., FIG. 6) to the head portion 112 due to the neck portion 114 maintaining a gap between the distal end of the head portion 112 and a surface of the bone. The neck portion 114 can flare at the transition regions of the neck portion 114 with the head portion 112 and the tapered body portion 116.

The tapered body portion 116 extends between the neck portion 114 and the slotted tail portion 118, and tapers distally towards the slotted tail portion 118. In embodiments, the tapered body portion 116 has a length "L1" extending at least a quarter of an overall length "L" of the outer member 110, and in some embodiments, the tapered body portion 116 has a length "L1" extending at least a half of the overall length "L" of the outer member 110. In certain embodiments, the tapered body portion 116 has a length "L1" that is less than a quarter of the overall length "L" of the fixation device 100. It should be understood that the tapered body portion 116 may have any shape, size, and/or length suitable for insertion into a targeted osseous tissue. For example, the fixation device 100 may be configured and dimensioned such that when the fixation device 100 is inserted into osseous tissue, such as a pedicle of a vertebra, the tapered body portion 116 fits within the pedicle.

The tapered body portion 116 includes helical threads 120 extending from an outer surface 116a of the tapered body portion 116 that are configured to cut and/or thread into osseous tissue. The helical threads 120 may extend the entire length "L1" of the tapered body portion 116, a portion of the length "L1" of the tapered body portion 116, or include regions of helical threads 120 disposed in spaced relation relative to each other along the length "L1" of the tapered body portion 116. The helical threads 120 can rotate clockwise or counter-clockwise about the tapered body portion 116. It should be understood that the configuration, number, and/or orientation of the helical threads 120 may vary depending upon, for example, the desired cutting and/or retaining characteristics desired of the fixation device 100.

In embodiments, the outer member 110 has a diameter "D1" ranging from about 2 mm to about 5 mm and, in some embodiments, the diameter "D1" of the outer member 110 ranges from about 3 mm to about 8 mm. In embodiments, the helical threads 120 have a major diameter "D2" ranging from about 6 mm to about 13 mm, and in some embodiments, the major diameter "D2" of the helical threads 120 ranges from about 6 mm to about 12 mm. In embodiments, the major diameter "D2" of the helical threads 120 tapers distally along the length "L1" of the tapered body portion 116 at a ratio of major diameter proximal "Dp" to major diameter distal "Dd" of about 1 to about 2, and in some embodiments, at a ratio of about 1.4 to about 1.7. The angle "α" of the taper, or taper angle, may vary and in embodiments, the taper angle "α" is from about 10 degrees to about 60 degrees and, in some embodiments, the taper angle "α" is from about 18 degrees to about 56 degrees.

The slotted tail portion 118 extends distally from the tapered body portion 116 to a distal end 110b of the outer member 110. In embodiments, the slotted tail portion 118 has a length "L2" extending at least a quarter of the overall length "L" of the outer member 110, and in some embodiments, the slotted tail portion 118 has a length "L2" extending at least a half of the overall length "L" of the outer member 110. The slotted tail portion 118 includes at least one slit 119 defined therein and, in embodiments, the slotted tail portion 118 includes at least two slits 119 defined therein that are positioned on opposed sides of the slotted tail portion 118. The at least one slit 119 extends longitudinally through the entire length "L2" of the slotted tail portion 118, or a portion of the length "L2" of the slotted tail portion 118 with the at least one slit 119 being open at the distal end 110b of the outer member 110.

The slotted tail portion 118 includes concentric arcs or ribs 122 extending from an outer surface 118a of the slotted tail portion 118. Each concentric arc 122 spans from one side of the slit 119 to another side of the slit 119, and in embodiments including two or more slits 119, each concentric arc 122 spans from one slit 119 to an adjacent slit 119 (e.g., from a slit 119 on a first side of the slotted tail portion 118 to another slit 119 on the opposite side of the slotted tail portion 118). Each concentric arc 122 includes a flat surface 122a and an angled surface 122b extending from an edge 122c of the flat surface 122a towards the central longitudinal axis "X" of the outer member 110. The concentric arcs 122 are configured and dimensioned to cut and/or thread into osseous tissue to provide improved fixation of the fixation device 100 into osseous tissue.

A central bore 111 extends through the outer member 110 and is concentric with the central longitudinal axis "X". As specifically shown in FIG. 1B, the central bore 111 is disposed distal of and in fluid communication with the opening 113 of the head portion 112, and extends through the head portion 112, the neck portion 114, the tapered body portion 116, and the slotted tail portion 118 such that the distal end 110b of the outer member 110 is open.

The central bore 111 is configured and dimensioned to receive the inner member 130 therein. The central bore 111 includes a proximal or first portion 111a dimensioned to accommodate a head 132 of the inner member 130, a central or second portion 111b dimensioned to accommodate a proximal shaft 134 of the inner member 130, and a distal or third portion 111c dimensioned to accommodate the expansion member 150.

The first portion 111a of the central bore 111 has a larger diameter than the second portion 111b of the central bore 111 and a smaller diameter than the opening 113 of the head portion 112. The first portion 111a of the central bore 111 is defined by a threaded inner surface 126 of the outer member 110 that is disposed distal of the inner surface 112b defining the opening 113 of the head portion 112. The first portion 111a of the central bore 111 is disposed within the head portion 112 of the outer member 110 and may extend at least partially into the neck portion 114 of the outer member 110.

The second portion 111b of the central bore 111 extends distally from the first portion 111a through the neck portion 114, the tapered body portion 116, and partially through the slotted tail portion 118. It should be understood that while the second portion 111b is shown having a constant diameter along the length thereof, the second portion 111b may have any suitable dimension configured to accommodate the inner member 130 therein.

The third portion 111c of the central bore 111 extends distally from the second portion 111b to the distal end 110b of the outer member 110. The third portion 111c has a varying diameter that can vary less than or larger than the diameter of the second portion 111b. The third portion 111c flares outwardly towards the distal end 110b of the outer member 110 to accommodate the expansion member 130 therein. It should be understood that the dimension of the third portion 111c may be configured to be complementary to the dimension of expansion members of various shapes and/or sizes.

Referring now to FIGS. 1B and 2, the inner member 130 includes a cap or head 132, an elongated or proximal shaft 134, a distal shaft 136, and a distal tip 138. The inner member 130 may be integrally formed (e.g., by machining, molding, etc.), or one or more of the head 132, the proximal shaft 134, the distal shaft 136, and/or the distal tip 138 may be fixedly attached (e.g., by welding, fastening, press-fitting, etc.) to an adjacent component of the inner member 130 such that the inner member 130 has a one-piece construction.

The inner member 130 is configured and dimensioned to fit within the central bore 111 of the outer member 110 and be concentric with the central longitudinal axis "X" of the outer member 110. The head 132 of the inner member 130 has a larger diameter than the proximal shaft 134, and is dimensioned to be received within the first portion 111a of the central bore 111 of the outer member 110. Specifically, the head 132 of the inner member 130 has a threaded outer surface 132a that is configured to threadingly engage the threaded inner surface 126 of the outer member 110 defining the first portion 111a of the central bore 111. The threaded inner surface 126 of the outer member 110 has a longitudinal length that is longer than a longitudinal length of the threaded outer surface 132a of the inner member such that the inner member 130 is longitudinally movable therein relative to the outer member 110, as described in further detail below. It should be understood, however, that the head 132 may have any size and/or shape that is capable of being retained within the first portion 111a of the central bore 111 and longitudinally movable therein.

The head 132 of the inner member 130 includes an opening 133 therein that is defined by an inner surface 132b of the head 132. The opening 133 is disposed at a proximal end 130a of the inner member 130 and is configured and dimensioned to receive a driving instrument (not shown). The inner surface 132b may be multi-faceted (e.g., hexagonal or hexolobular in shape), keyed, or any other suitable configuration that is engageable with a suitable driving instrument to enable the driving instrument to control rotation of the inner member 130 and/or aid in the insertion of the fixation device 100 into osseous tissue.

The proximal shaft 134 of the inner member 130 is sized and shaped to fit within the second portion 111b of the central bore 111 of the outer member 110, and may extend at least partially into the third portion 111c of the central bore 111. The proximal shaft 134 has an outer dimension that is complementary to the inner dimension of the second portion 111b of the central bore 111 of the outer member 110 to aid in supporting and maintaining alignment of the inner member 130 within the outer member 110 during rotation of the inner member 130. Accordingly, the proximal shaft 134 may have any size and/or shape complementary to the geometry of the second portion 111b of the central bore 111 of the outer member 110.

The distal shaft 136 of the inner member 130 is sized and shaped to fit within the expansion member 150 which, in turn, is sized and shaped to be received within the third portion 111c of the central bore 111 of the outer member 110. The distal shaft 136 has a smaller diameter than the proximal shaft 134, however, it should be understood that the distal shaft 136 may have the same or larger diameter than the proximal shaft 134 so long as the distal shaft 136 is securable within the expansion member 150. The distal shaft 136 may be secured within the expansion member by, for example, friction fit, welded connection, threaded attachment, among other fastening techniques within the purview of those skilled in the art.

The distal tip 138 of the inner member 130 extends distally through the expansion member 150 and includes a pointed end 138a. Other configurations of the distal tip 138 are contemplated. For example, the distal tip 138 be blunt and/or configured to be flush with a distal end 152c of a body 152 of the expansion member 150 for atraumatic insertion into osseous tissue.

As shown in FIGS. 1B and 3, the expansion member 150 includes a body 152 having a generally tear drop shape including a first diameter at a proximal portion 152a of the body 152 and a second diameter at a distal portion 152b of the body 152 that is wider than the first diameter. A bore 153 extends through the entire length of the body 152 and is configured and dimensioned to receive the distal shaft 136 of the inner member 130 therein. A distal end 152c of the body 152 may be semispherical in shape and/or atraumatic to aid in guiding the fixation device 100 through osseous tissue. It should be understood that the expansion member 150 can be of any size and/or shape so long as it capable of distending or expanding the slotted tail portion 118 of the outer member 110 (e.g., at least a portion of the expansion member has a larger diameter than the diameter of the third portion of the central bore).

With reference again to FIGS. 1A and 1B, the fixation device 100 has an initial or unexpanded position in which the head 132 of the inner member 130 is positioned within the first portion 111a of the central bore 111 with the outer threaded surface 132a of the head 132 engaged with a distal section 126a of the threaded inner surface 126 of the central bore 111, and the expansion member 150 is positioned within the third portion 111c of the central bore 111 within the slotted tail portion 118 such that the slotted tail portion 118 is in an undistended configuration (e.g., the proximal portion of the expansion member is flush or abuts an inner surface of the slotted tail portion and the distal portion of the expansion member is distal of the slotted tail portion).

The fixation device 100 is movable from the unexpanded position to a deployed or expanded position, as shown in FIGS. 4A and 4B, by rotating the inner member 130 with respect to the outer member 110 to move the inner member 130 longitudinally relative to the outer member 110. The head 132 of the inner member 130 is engaged with a driving instrument (not shown) to rotate and move the head 132 proximally within the first portion 111a of the central bore 111 such that the threaded outer surface 132a of the head 132 engages a proximal section 126b (FIG. 1B) of the threaded inner surface 126 of the first portion 111a of the central bore 111. The expansion member 150, which is secured to the distal shaft 126 of the inner member 130, moves with the inner member 130 proximally into the third portion 111c of the central bore 111 to distend the slotted tail portion 118. The expansion member 150 has a larger dimension than that of the third portion 111c of the central bore 111 such that the expansion member 150 applies a radial force to the slotted tail portion 118 to laterally displace the slotted tail portion 118 from the undistended configuration to a distended configuration.

In a method of using the fixation device 100 in accordance with an embodiment of the present disclosure, an insertion hole is formed in osseous tissue. A clinician drills or otherwise forms a hole into osseous tissue using known devices and techniques (e.g., punching, cutting, coring, etc.). For example, an insertion hole may be formed by preparing the surface of the osseous tissue with a burr or other like instrument and then using an awl or other like instrument to start the hole in such anatomy as a pedicle of a vertebra. The fixation device 100, disposed in the unexpanded position of FIGS. 1A and 1B, is then inserted into the insertion hole. A driving instrument (not shown) may be inserted into the opening 113 of the head portion 112 of the outer member 110 to engage the inner surface 112b of the opening 113 to aid in the insertion of the fixation device 100 into the insertion hole. The clinician inserts the fixation device 100 into the insertion hole until the tapered body portion 116 is disposed within the bone (e.g., a pedicle of a vertebra).

Once the fixation device 100 is inserted into the osseous tissue, the inner member 130 of the fixation device 100 is manipulated by imparting a rotation force thereto to move the fixation device 100 from the unexpanded position to the expanded position shown in FIGS. 4A and 4B. As discussed above, a clinician can affix a driving instrument (not shown)

through the opening 113 defined in the head portion 112 of the outer member 110 and into the opening 133 defined in the head 132 of the inner member 130 and apply a force to the driving instrument that can rotate the inner member 130 about the central longitudinal axis "X" within the outer member 110 so that the outer threaded surface 132a of the head 132 of the inner member 130 engages with the threaded inner surface 126 of the central bore 111. In this manner, the inner member 130 moves proximally within the outer member 110 so that the expansion member 150, which is affixed to the inner member 130, distends the slotted tail portion 118 of the outer member 110. This increases a diameter of the slotted tail portion 118 defining an inverted conical configuration.

In the expanded position, the slotted tail portion 118 of the outer member 110 may have an elliptical shape that fills the space within the pedicle, and/or the concentric arcs 122 of the slotted tail portion 118 can engage with the osseous tissue. In situations where the fixation device 100 is used in a vertebra, the slotted tail portion 118 engages osseous tissue just below the isthmus of the pedicle to improve the fixation of the fixation device 100 into the osseous tissue.

The outer member 110 of the fixation device 100 may also be manipulated by imparting a rotational force thereto. A rotational force may be applied to the outer member 110 (e.g., to the head portion 112) by placing a driving instrument (not shown) into the opening 113 of the head portion 112 of the outer member 110 to engage the inner surface 112b of the opening 113 and applying a force to the driving instrument that can rotate the outer member 110 about the central longitudinal axis "X" so that the helical threads 120 of the tapered body portion 116 engage with the osseous tissue (e.g., the pedicle). While driving instruments (not shown) are described for driving the outer and inner members 110, 130, it is contemplated that a single driving instrument having coaxial and independently drivable shafts may be utilized with the fixation device 100 of the present disclosure in lieu of two separate driving instruments.

One of ordinary skill in the art will appreciate that any combination of manipulating the inner and outer members 130, 110 of the fixation device 100 can be used to secure, cut, and/or thread the fixation device 100 into the osseous tissue at the insertion site. Further, a clinician can apply an opposite rotational force to the inner and/or outer members 130, 110 of the fixation device 100 to adjust the placement of the fixation device 100 within the osseous tissue or to remove the fixation device 100 completely therefrom.

Figure 5A:
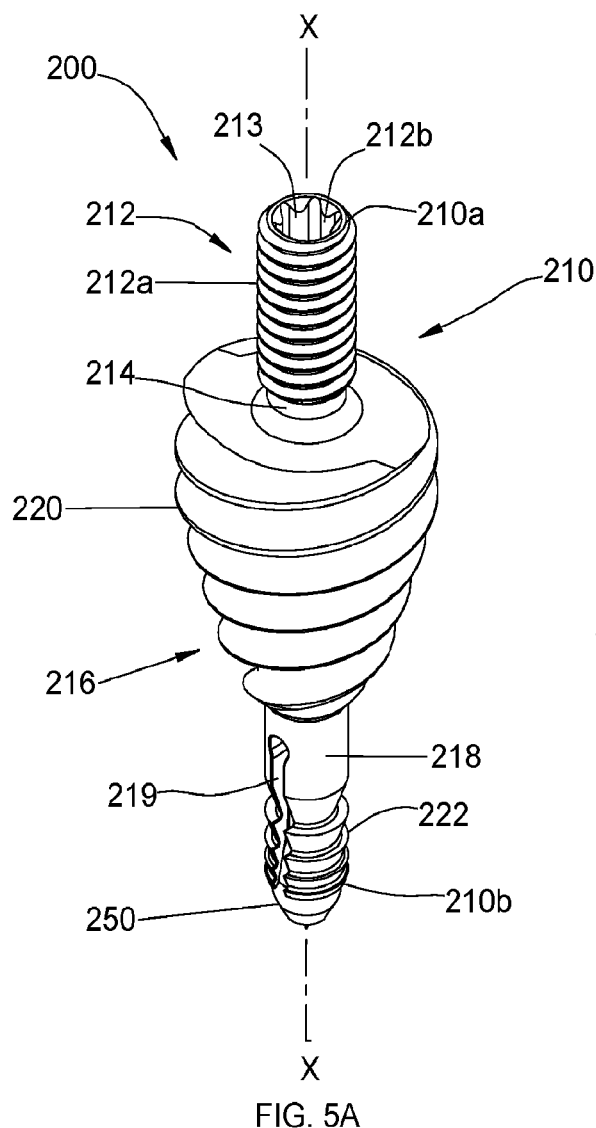
FIG. 5A is a perspective view of a fixation device in accordance with another embodiment of the present disclosure, shown in an unexpanded position.
Figure 5B:
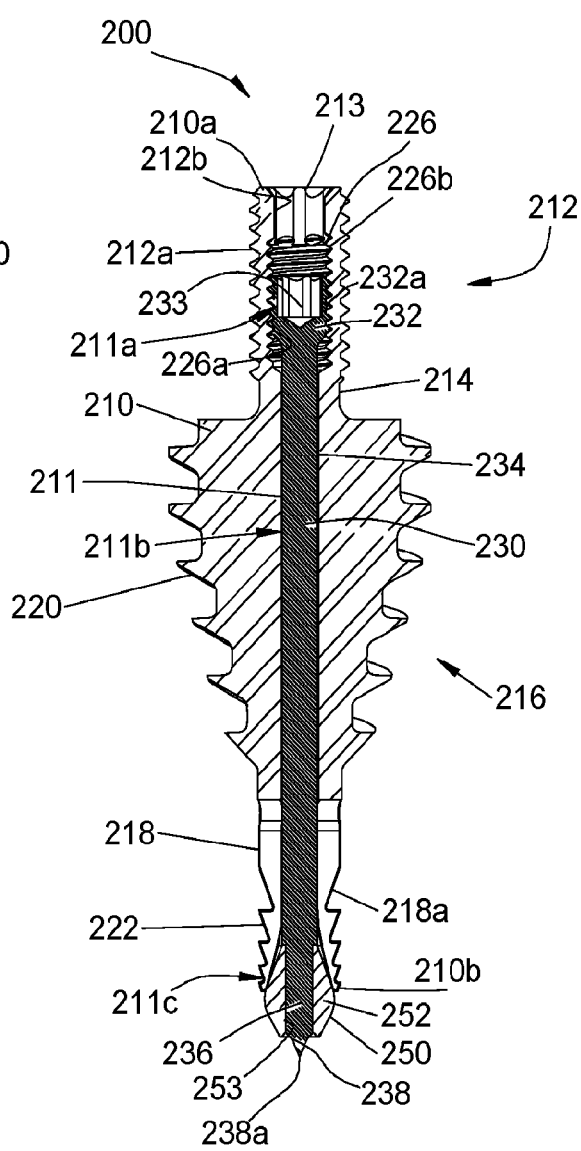
FIG. 5B is a cross-sectional view of the fixation device of FIG. 5A.

With reference now to FIGS. 5A and 5B, a fixation device 200 in accordance with another embodiment of the present disclosure is shown. The fixation device 200 is substantially similar to the fixation device 100 and will be discussed with respect to the differences therebetween.

The fixation device 200 includes an outer member or post 210, an inner member or pin 230, and an expansion member or bulb 250. The outer member 210 extends along a central longitudinal axis "X" and includes a head portion 212, a neck portion 214, an elongate or tapered body portion 216, and a slotted tail portion 218.

The head portion 212 of the outer member 210 has a substantially cylindrical shape, and includes a threaded outer surface 212a that is configured for attachment of a complementary inner threaded attachment device (e.g., a modular attachment assembly). The head portion 212 includes an opening 213 therein that is defined by an inner surface 212b of the head portion 212. The opening 213 is disposed at a proximal end 210a of the outer member 210 and is configured and dimensioned to receive a driving instrument (not shown).

The neck portion 214 extends between the head portion 212 and the tapered body portion 216. The tapered body portion 216 extends between the neck portion 214 and the slotted tail portion 218, and tapers distally towards the slotted tail portion 218. The tapered body portion 216 includes exterior helical threads 220 configured to cut and/or thread into osseous tissue.

The slotted tail portion 218 extends distally from the tapered body portion 216 to a distal end 210b of the outer member 210. The slotted tail portion 218 includes at least one slit 219 defined therein and concentric arcs 222 extending from an outer surface 218a of the slotted tail portion 218 that are configured and dimensioned to cut and/or thread into osseous tissue.

A central bore 211 extends through the outer member 210 and is concentric with the central longitudinal axis "X". The central bore 211 is configured and dimensioned to receive the inner member 230 therein. The central bore 211 includes a proximal or first portion 211a dimensioned to accommodate a head 232 of the inner member 230, a central or second portion 211b dimensioned to accommodate a proximal shaft 234 of the inner member 230, and a distal or third portion 211c dimensioned to accommodate the expansion member 250.

The first portion 211a of the central bore 211 is defined by a threaded inner surface 226 that is disposed distal of the inner surface 212b defining the opening 213 of the head portion 212. The second portion 211b of the central bore 211 extends distally from the first portion 211a and the third portion 211c of the central bore 211 extends distally from the second portion 211b to the distal end 210b of the outer member 210.

The inner member 230 includes a cap or head 232, an elongated or proximal shaft 234, a distal shaft 236, and a distal tip 238. The head 232 of the inner member 230 is dimensioned to be received within the first portion 211a of the central bore 211 of the outer member 210 and includes a threaded outer surface 232a that is configured to threadingly engage the threaded inner surface 226 defining the first portion 211a of the central bore 211. The head 232 of the inner member 230 includes an opening 233 defined therein that is configured and dimensioned to receive a driving instrument (not shown).

The proximal shaft 234 of the inner member 230 is sized and shaped to fit within the second portion 211b of the central bore 211 of the outer member 210, and the distal shaft 236 of the inner member 230 is sized and shaped to fit within the expansion member 250 which, in turn, is sized and shaped to be received within the third portion 211c of the central bore 211 of the outer member 210. The distal tip 238 of the inner member 230 extends distally through the expansion member 250 and includes a pointed end 238a.

The expansion member 250 includes a body 252 having a tear drop shape and a bore 253 extending through the entire length of the body 252 that is configured and dimensioned to receive the distal shaft 236 of the inner member 230 therein.

The fixation device 200 has an initial or unexpanded position in which the head 232 of the inner member 230 is positioned within the first portion 211a of the central bore 211 with the outer threaded surface 232a of the head 232 engaged with a distal section 226a of the threaded inner surface 226 of the central bore 211, and the expansion member 250 is positioned within the third portion 211c of the central bore 211 within the slotted tail portion 218 such that the slotted tail portion 218 is in an undistended configuration.

The fixation device 200 is movable from the unexpanded position to a deployed or expanded position (not shown) by rotating the inner member 230 with respect to the outer member 210 such that the head 232 of the inner member 230 moves proximally within the first portion 211a of the central bore 211 and the outer threaded surface 232a of the head 232 engages a proximal section 226b of the threaded inner surface 226 of the central bore 211. The expansion member 250, which is secured to the distal shaft 226 of the inner member 230, moves with the inner member 230 proximally into the third portion 211c of the central bore 211 to distend the slotted tail portion 218.

The fixation device 200 is positioned within and secured to osseous tissue in a similar manner as discussed above with regard to fixation device 100. Both embodiments are fully inserted into osseous tissue with minimal and/or reduced time and/or effort compared to traditional bone screws. The expandable or distendable distal regions of the fixation devices 100, 200 provide, for example, increased securement while allowing for less bone removal and/or use of a fixation device having a shorter length that allows the clinician greater flexibility during a surgical procedure and reduced risk of damaging surrounding tissue by means of reducing how much anatomy must be traversed by the clinician. The expandable distal regions allow for additional fixation and increased pull out strength after traversal of anatomy that can be challenging for a clinician to traverse, such as a pedicle of a vertebra.

Figure 6:
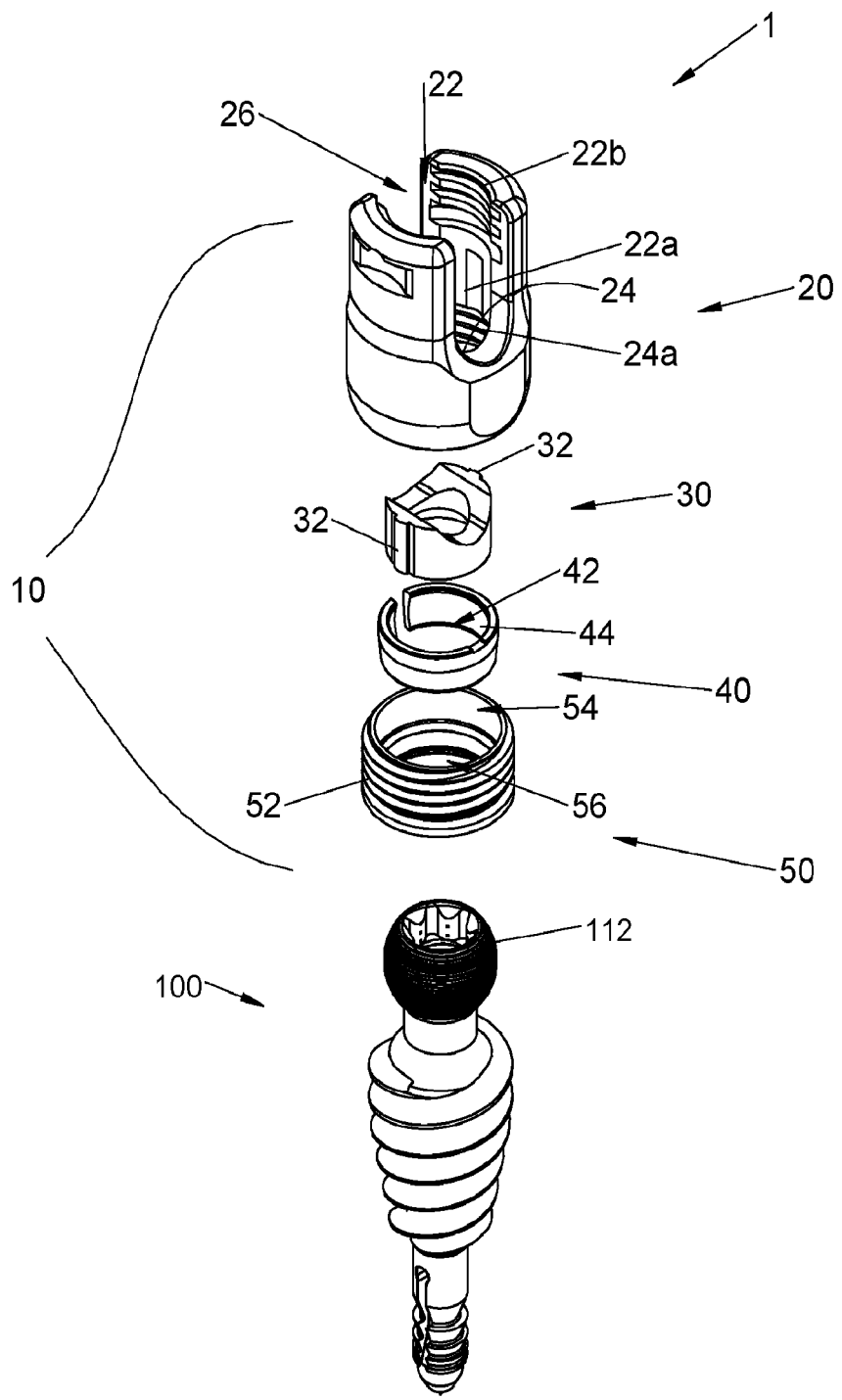
FIG. 6 is a perspective view of the fixation device of FIG. 1A and a modular head assembly, with parts separated, in accordance with an embodiment of the present disclosure.

In embodiments, a surgical device, such as a modular head assembly 10 as shown in FIG. 6, may be coupled to the fixation device 100 such that other surgical devices (e.g., rods, plates, etc.) may be coupled thereto. FIG. 6 illustrates a surgical fixation system 1 including the modular head assembly 10 and the fixation device 100. The modular head assembly 10 includes a housing 20, an anvil 30, a snap ring 40, and an insert 50. The modular head assembly 10 is assembled by aligning a pair of tabs 32 of the anvil 30 with a corresponding pair of slots 22a of a through-hole 22 of the housing 20, and advancing the anvil 30 in a proximal direction within the through-hole 22 such that the pair of tabs 32 engage the pair of slots 22a. Next, the snap ring 40 is placed adjacent a counterbore 24 of the housing 20 and advanced in a proximal direction such that the snap ring 40 is slidably received therein. With the snap ring 40 received within the counterbore 24, the insert 50 is initially placed adjacent the counterbore 24 of the housing 20, and then rotated in a first direction such that a plurality of threads 52 of the insert 50 threadably engages a corresponding plurality of threads 24a of the counterbore 24 of the housing 20. The insert 50 is further rotated until the insert 50 is fully received within the counterbore 24. In this position, the anvil 30 is in a proximal most position and the snap ring 40 is disposed within a first counterbore 54 of the insert 50 such that the snap ring 40 is in a first, uncompressed state.

With the fixation device 100 inserted into bone, as discussed above, the assembled modular head assembly 10 is placed adjacent the head portion 112 of the fixation device 100. The modular head assembly 10 is then advanced in a distal direction such that the head portion 112 of the fixation device 100 is received within a bore 56 of the insert 50, and thereafter, within a lumen 42 of the snap ring 40. As the head portion 112 of the fixation device 100 advances within the lumen 42 of the snap ring 40, the head portion 112 causes the snap ring 40 to expand (e.g., the diameter enlarges) to accept the head portion 112 therein. A concave inner surface 44 of the lumen 42 conforms to the spherical profile of the head portion 112 such that the diameter of the snap ring 40 reduces from an expanded state during insertion of the head portion 112 therein to a compressed state where the inner diameter of the lumen 42 conforms to the diameter of the head portion 112 and provides a compressive force thereon. Thereafter, the axial orientation of the fixation device 100 relative to the modular head assembly 10 may be adjusted and locked, for example, when a suitable spinal rod (not shown) is secured within a U-shaped slot 26 of the housing 20 using a suitable set screw (not shown) threadingly engaged with a plurality of threads 22b of the through-hole 22 of the housing 20.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown and described in connection with certain embodiments may be combined with the elements and features of certain other embodiments without departing from the scope of the present disclosure, and that such modifications and variation are also included within the scope of the present disclosure. Accordingly, the subject matter of the present disclosure is not limited by what has been particularly shown and described. Thus, other embodiments are within the scope of the following claims.

What is claimed is:

1. A fixation device comprising:
an outer member including an elongated body portion, a slotted tail portion, an unthreaded portion proximal to and adjacent the slotted tail portion, the outer member including helical threads tapering toward the unthreaded portion and defining a central bore therethrough extending along a central longitudinal axis, the slotted tail portion including concentric arcs extending perpendicular to the central longitudinal axis, and a head portion extending proximal to the helical threads and defining an opening therein in fluid communication with the central bore;
an inner member disposed within the central bore of the outer member; and
an expansion member coupled to the inner member, wherein proximal movement of the inner member relative to the outer member moves the expansion member into the slotted tail portion of the outer member such that the slotted tail portion moves from an undistended configuration to a distended configuration.

2. The fixation device according to claim 1, wherein the inner member is disposed within the central bore distal to the opening defined in the head of the outer member, the inner member movable longitudinally within the central bore.

3. The fixation device according to claim 1, wherein the elongated body portion of the outer member tapers distally towards the slotted tail portion.

4. The fixation device according to claim 3, wherein the elongated body portion includes helical threads disposed on an outer surface of the elongated body portion.

5. The fixation device according to claim 1, wherein the slotted tail portion includes at least one slit defined therein.

6. The fixation device according claim 5, wherein the at least one slit extends longitudinally through at least a portion of a length of e slotted tail portion and is open at a distal end of the outer member.

7. The fixation device according to claim 5, wherein the at least one slit of the slotted tail portion includes two slits disposed on opposed sides of the slotted tail portion.

8. The fixation device according to claim 5, wherein the slotted tail portion includes concentric arcs extending from an outer surface of the slotted tail portion.

9. The fixation device according to claim 1, wherein the central bore includes a first portion, a second portion having a diameter smaller than a diameter of the first portion, and a third portion having a varying diameter.

10. The fixation device according to claim 1, wherein the inner member icludes a head, a proximal shaft, and a distal shaft.

11. The fixation device according to claim 10, wherein the head of the inner member is positioned within a first portion of the central bore, the proximal shaft is positioned within a second portion of the central bore, and the distal shaft is secured within the expansion member, the expansion member positionable within a third portion of the central bore.

12. The fixation device according to claim 11, wherein the inner member includes a distal tip, the distal tip extending distally through the expansion member.

13. The fixation device according to claim 11, wherein the head of the inner member includes a threaded outer surface threadingly engaged with a threaded inner surface of the outer member defining the first portion of the central bore.

14. The fixation device according to claim 1, wherein the expansion member includes a body having a proximal portion and a distal portion, a diameter of the distal portion being wider than a diameter of the proximal portion, and wherein, when the slotted tail portion is in the distended configuration, the distal portion of the expansion member exerts a radial force on the slotted tail portion.

15. A method of securing a fixation device to osseous tissue, comprising:
    inserting an elongated body portion, a slotted tail portion, and an unthreaded portion proximal to and adjacent the slotted tail portion of an outer member of a fixation device into a hole in osseous tissue, the slotted tail portion disposed in an undistended configuration, the outer member defining a central bore therethrough extending along a central longitudinal axis, the slotted tail portion including concentric arcs extending perpendicular to the central longitudinal axis, and the outer member defining a head portion extending proximal to helical threads, the head defining an opening therein in fluid communication with the central bore;
    applying a rotational force to the outer member to engage the helical threads disposed on an outer surface of the elongated body portion with the osseous tissue, the helical threads tapering distally toward the unthreaded portion; and
    applying a force to an inner member of the fixation device that is disposed within the central bore of the outer member, the inner member coupled to an expansion member such that the force applied to the inner member moves the expansion member proximally into the slotted tail portion to move the slotted tail portion to a distended configuration.

16. The method according to claim 15, wherein applying the force to the inner member includes rotating the inner member.

* * * * *